United States Patent [19]

Toms, II

[11] Patent Number: 4,581,599
[45] Date of Patent: Apr. 8, 1986

[54] NUCLEAR RADIATION APPARATUS AND METHODS FOR SURVEYING PHYSICAL CHARACTERISTICS AND PROPERTIES

[75] Inventor: Thomas M. Toms, II, Raleigh, N.C.

[73] Assignee: Troxler Electronic Laboratories, Inc., Research Triangle Park, N.C.

[21] Appl. No.: 346,172

[22] Filed: Feb. 5, 1982

[51] Int. Cl.$^4$ .............................................. G08B 21/00
[52] U.S. Cl. ............................... 340/286 M; 250/253; 364/420
[58] Field of Search ............... 340/286 M, 286 R, 525; 364/420, 178; 250/253

[56] References Cited

U.S. PATENT DOCUMENTS

| | | | |
|---|---|---|---|
| 2,986,638 | 5/1961 | Lee | 250/253 |
| 3,354,310 | 11/1967 | Swift | 250/253 |
| 4,322,805 | 3/1982 | Rog et al. | 364/420 |
| 4,365,191 | 12/1982 | Weldon et al. | 324/348 |
| 4,381,544 | 4/1983 | Stamm | 364/420 |

*Primary Examiner*—Glen R. Swann, III
*Attorney, Agent, or Firm*—Bell, Seltzer, Park & Gibson

[57] ABSTRACT

An area is surveyed for variation in a physical characteristic or property which is effective for modifying nuclear radiation of a predetermined type through the use of an apparatus and in accordance with a method in which the modifying characteristic is measured by applying nuclear radiation while generating a signal representative of the measured characteristic, the generated signal is registered in the programmable memory device, the steps of measuring while generating and registering are thereafter repeated, and the information gathered is transmitted for retrieval and processing at a remote location.

12 Claims, 5 Drawing Figures

NUCLEAR RADIATION APPARATUS AND METHODS FOR SURVEYING PHYSICAL CHARACTERISTICS AND PROPERTIES

FIELD AND BACKGROUND OF INVENTION

Nuclear radiation gauges have been and are being employed for measuring physical characteristics and properties of materials. Specific examples include the use of nuclear radiation gauges to measure thickness, density, and moisture content. In applications in which such measurements are to be made while surveying an area for variations across the area, typical processes involve defining a grid to be applied to the area to be surveyed, and then measuring the characteristic or property at a plurality of points in the grid while noting the measurement readings. Thereafter, necessary calculations and mapping can be performed from field notes. Other types of applications may involve registering variations over time, particularly with respect to moisture content. Applications in which such techniques have met with some success include surveying land areas such as fields for moisture content, surveying construction site areas such as airport runways for density, and surveying road construction projects for thickness of paving materials applied.

While surveying practices such as those mentioned above have achieved some acceptance in at least certain fields, such practices are subject to operator error and are time-consuming. As a consequence, access to the result of a survey conducted using a nuclear radiation gauge and as described above is usually delayed.

BRIEF DESCRIPTION OF INVENTION

With the aforementioned difficulties and deficiencies of prior methods and apparatus particularly in mind, it is an object of the present invention to survey for a physical characteristic or property, such as for example surveying for density, thickness, or moisture content, by measuring the desired physical characteristic at a predetermined location being surveyed while generating a digital signal representative of the measured characteristic, registering a generated signal in a programmable memory device, repeating the steps of measuring while generating and registering at successive locations distributed in a predetermined array so as to build a file, and thereafter transmitting the registered signals from the gauge, wherever located, to a remote location for processing. By proceeding in the manner described, an operator may move quickly from location to location, minimizing the time required to conduct the survey. Additionally, the possibility of operator error is significantly reduced or entirely eliminated.

Yet a further object of this invention is to map a surveyed area for the physical characteristic or property under test by conducting a survey as briefly described above using a nuclear radiation gauge, transmitting the registered signals from the gauge, and thereafter processing the registered signals and generating from the processed signals a map display of the area surveyed and of the property or characteristic at the locations of the survey. It is contemplated by the present invention that such retrieval, processing and generating of a display may be accomplished through the use of a digital computer, thereby expediting access to the result of the survey while decreasing or entirely eliminating the possibility of operator error.

Yet a further object of the present invention is to provide, for use by an appropriately trained operator, a nuclear radiation gauge for surveying the characteristics or properties of an area such as a field or the like. In accordance with the present invention, the gauge incorporates an appropriate nuclear radiation source, one or more detectors, and signal registering and storing circuitry operatively connected with the detectors for registering signals representative of the characteristic or property for which the survey is being conducted and storing registered signals in a programmable memory device. A central processor unit, forming a portion of the signal registering and storing circuitry, directs the registering and storing of signals and the actions of an operator. By the provision of a gauge as contemplated by the present invention, surveying is simplified for an operator in that the operator need only move from location to location in a predetermined array and as directed, positioning the gauge at each location, and awaiting completion of a gauge-determined time interval for measurement at each location. The operator of the gauge in accordance with the present invention is relieved of the necessity of maintaining field notes of each reading as the readings are taken.

BRIEF DESCRIPTION OF DRAWINGS

Some of the objects of the invention having been stated, other objects will appear as the description proceeds, when taken in connection with the accompanying drawings, in which.

DETAILED DESCRIPTION OF INVENTION

While the present invention will be described more fully hereinafter with reference to the accompanying drawings, in which a preferred embodiment of the present invention is shown, it is to be understood at the outset of the description which follows that persons of skill in the appropriate arts may modify the invention here described while still achieving the favorable results of this invention. Accordingly, the description which follows is to be understood as being a broad, teaching disclosure directed to persons of skill in the appropriate arts, and not as limiting upon the present invention.

Figure 1:
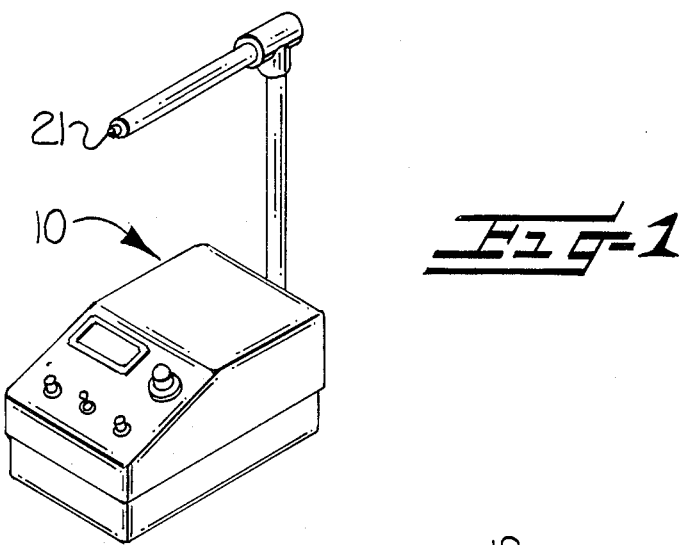
FIG. 1 is a perspective view of a gauge embodying the present invention.
Figure 2:
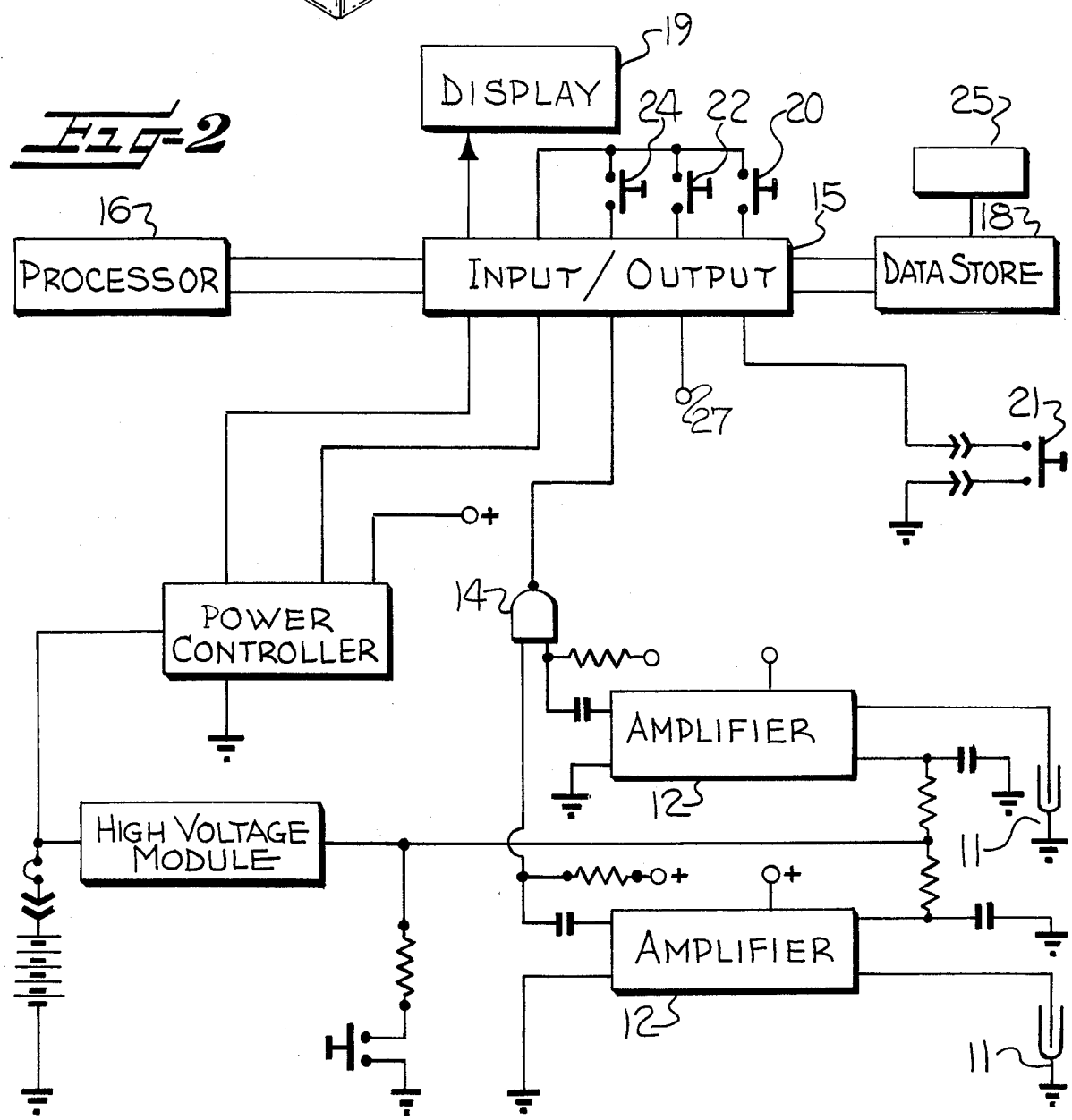
FIG. 2 is a schematic representation of components of a gauge in accordance with the present invention.

A gauge in accordance with the present invention, as generally indicated at 10 in FIG. 1, may comprise a case containing a radioactive source, detectors, electronic modules, and rechargeable battery packs. As is known to persons familiar with such gauges and skilled in their use, appropriate switches, keyboards, indicators and displays may be provided, as well as handles or the like for the manipulation of the gauge.

Gauges as contemplated by the present invention may operate using a variety of specific types of nuclear radiation and a variety of radiation modification effects. By way of example, the density of soil and of other materials may be measured by the moderating effect of the soil and the like upon high energy gamma radiation emitted from an appropriate source such as radium or cesium 137. Such measurements may be done by a direct transmission technique in which detectors respond to the reduction in energy level of gamma photons due to transmission of the photons through the material undergoing test, or may be measured using a backscatter technique in which shielding substantially blocks off direct transmission between a radiation source and detector, so that the detector responds to radiation reflected from the material under test to the detectors or "backscattered." The uses of such sources and techniques, and particular gauges constructed and adapted for such measurements, will be familiar to persons of appropriate skill in the applicable arts. Similarly, nuclear radiation moisture gauges will be familiar to persons of appropriate skill in the arts applicable to the present invention. In such gauges, hydrogen moderation of high energy neutrons emitted from an appropriate source such as Americium −241 and Beryllium and detection of moderated, thermal neutrons are employed. As pointed out in the discussion which follows, the present invention is contemplated as being useful with all of such types of gauges, sources, detectors and techniques.

For purposes of the present discussion, it will be first assumed that the gauge 10 of FIG. 1 is a surface density measuring gauge employing gamma radiation backscatter techniques. Such a gauge may be employed, by way of example only, for surveying soil density in a construction site area such as an airport taxiway or hardstand. In such a specific example, the desired measurement would be the soil density within a defined area on which a defined grid of measurement locations may be established, and measurement may proceed as described more fully hereinafter. The present invention contemplates that the gauge 10 include detectors and signal registering and storing means operatively connected with the detectors and responsive thereto for accomplishing several functions in accordance with the present invention. Signals generated by detectors 11 are received and amplified by corresponding amplifiers 12 and then gated through a gate device 14 for delivery to input/output circuitry generally indicated at 15. The input/output circuitry 15 serves to coordinate the functions of a number of other components of the gauge 10 in accordance with the present invention, including a central processing unit 16, a data store unit 18, and a display 19.

The input/output circuitry 15 is connected with a start switch 20 which may be mounted on the instrument case and with a remote start switch 21 which may be mounted on a handle for ready manipulation by an operator. Additionally, the input/output circuitry is connected with an increment switch 22 and a decrement switch 24, the functions of which are described more fully hereinafter.

The data store circuitry 18 is operatively connected with a socket 25 for removably retaining a memory storage device of the type known as an Erasable Programmable Read-Only Memory or EPROM. As known to persons skilled in the arts of programmable memory devices, an EPROM is a device which may be erased by exposure to ultraviolet light or the like and may thereafter have digital data entered thereinto. In the present invention, the EPROM provides a means for registering signals and thereafter, by removing and transporting the EPROM only, transmitting the registered signals for retrieval at a remote location at which a central processing unit may process the registered signals and generate from the processed signals a map display of the area surveyed and the physical characteristic properties at each of the grid locations within the area.

As will be appreciated, an EPROM provides, as described hereinabove, a means for transmitting data. The present invention contemplates that the means for transmitting data may take other forms including, by way of example only, an electrically eraseable PROM, magnetic media devices such as tape cassettes, and interface transmitting devices such as those known as MODEMs. Where some other type of data transmitting means is employed, the data store circuitry 18 either may incorporate such a provision directly (such as by the inclusion of an acoustic coupler for a telephone handset) or may be provided with an appropriate socket for removably retaining a connector to such a transmittal device.

In the form preferred, the display 19 takes the form of a liquid crystal display which is capable of presenting a range of alphanumeric information under the control of the processor 16 and through the input/output circuits 15.

Figure 3A:
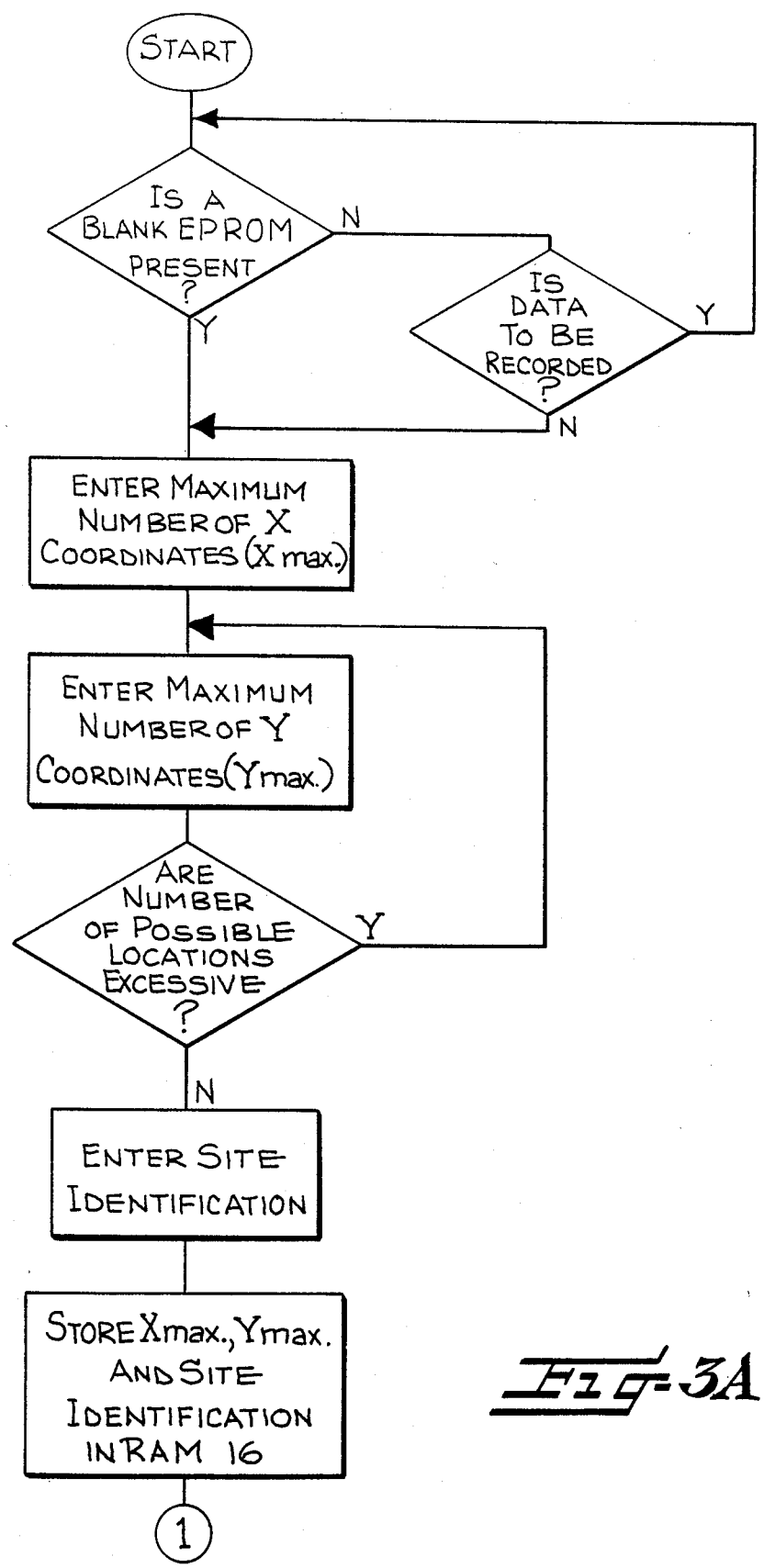
FIGS. 3A-3C are a flowchart illustrating a method for surveying an area in accordance with the invention.
Figure 3B:
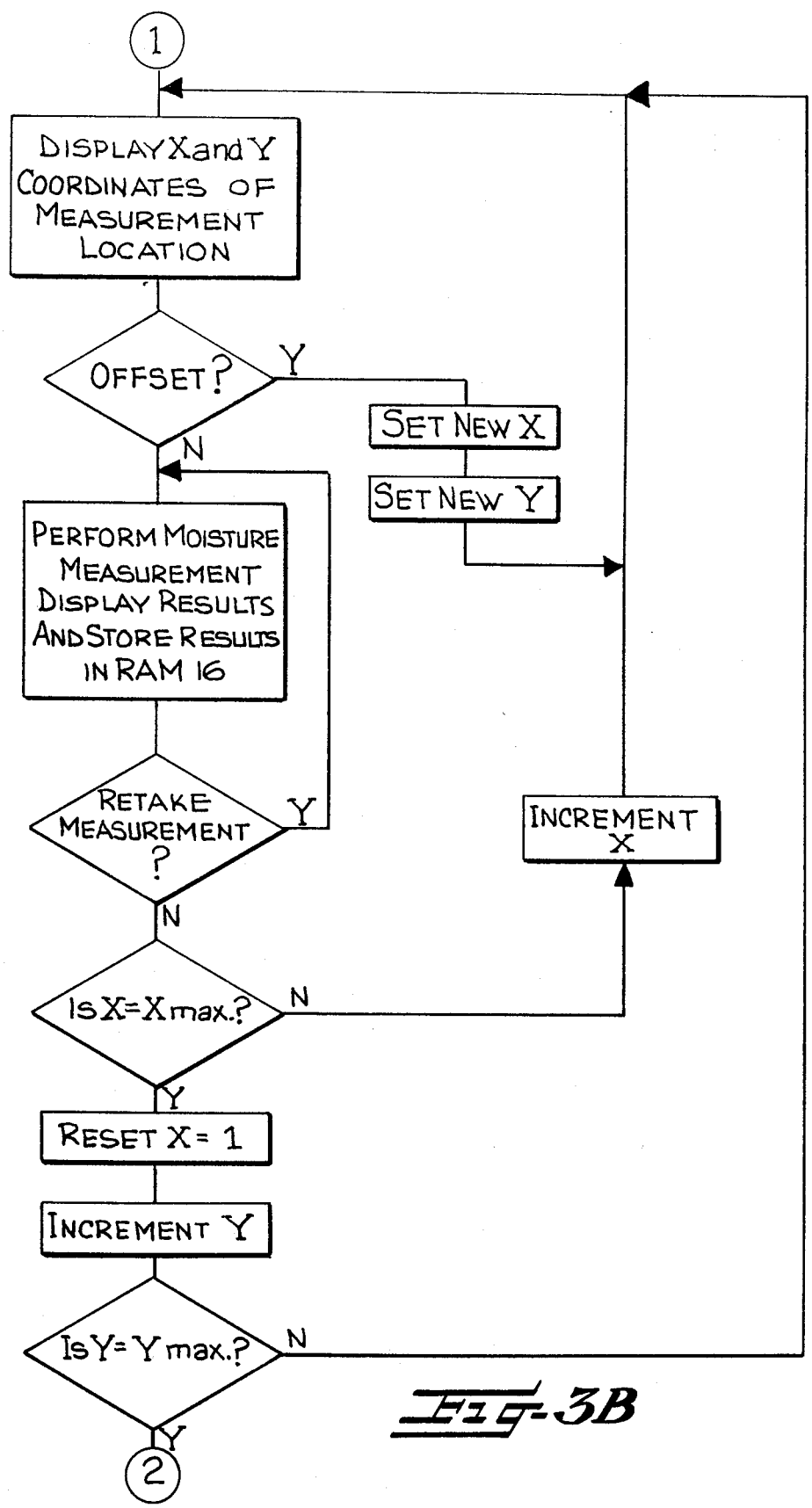
Figure 3C:
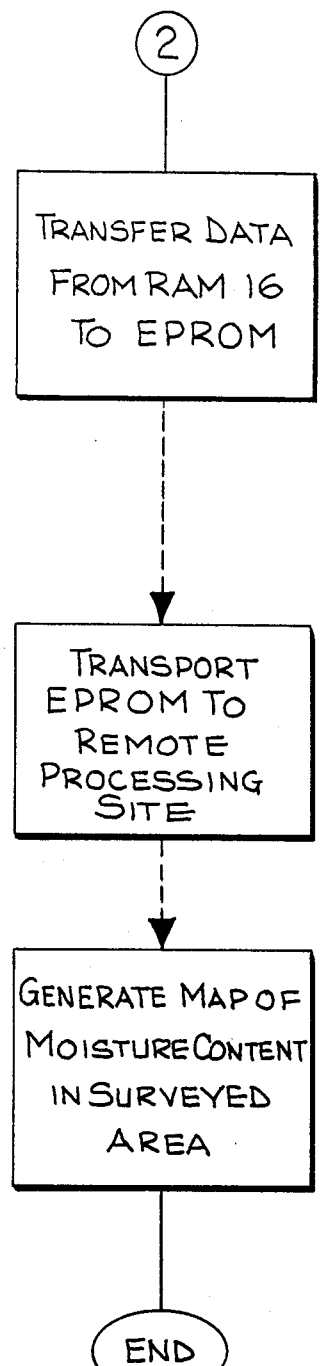

In gauges in accordance with the present invention, the processor circuitry 16 performs a variety of functions. A number of those functions will now be described in connection with FIGS. 3A–3C in the context of use of the gauge in surveying a paving construction area for soil density. It is to be understood that the specific description given is contemplated as making possible a more general application of the principles here described. It is assumed that an area to be surveyed is available, and that the gauge has been turned on, and a desired time interval for each measurement selected. Thereafter, upon an operator manipulating the controls for the gauge, the processor 16 will determine whether or not a blank EPROM is present in the socket 25. If a blank EPROM is present, then the gauge will display on the display 19 an inquiry asking for the coordinates of the area to be surveyed. Coordinates are specified as X and Y coordinates and are for a grid having a number of locations beginning from $X=1$ and $Y=1$ and continuing to such numbers as are required for the area to be surveyed. As will be appreciated, such a $(X, Y)=(n, n)$ coordinate system may extend to such a number of specific locations as may be accommodated in the specific memory devices chosen. Thus, the selection of limits upon the coordinates may be left to the person of appropriate skill in the applicable arts. In an operating model of a gauge in accordance with the present invention, the maximum number allowed for either maximum X or maximum Y is 999 and the number of available memory locations is 3961.

Should the processor circuitry 16 discover that no EPROM is present in the socket 25 (where the gauge is so programmed), then an inquiry will be displayed on the display 19 asking if data is to be recorded. A "yes" response would require the insertion of a blank EPROM into the socket 25 before the processor circuitry 16 would permit the operations to continue. A "no" response would permit the programming within the processor circuitry 16 to continue, due to an indication of operator awareness that data will not be transferred into an EPROM. The operator may suitably indicate a yes or no response by depressing an appropriate switch provided on the instrument. For example, a positive (yes) response may be indicated by depressing the increment switch 22 and a negative (no) response by depressing the decrement switch 24. This programming review of the presence of a removable memory device may be varied where other means of transmitting information is employed.

Upon the gauge reaching the programming point of asking for a maximum value of X, by either programming path described above, the operator must then enter a maximum value of X for the predetermined array of predetermined locations in the area to be surveyed. Such a value is entered by actuating the increment switch 24 until such time as the display 19 displays an appropriate number. The decrement switch 22 operates in a similar fashion, should there be an incorrect display. When the operator has manipulated the gauge so that the display 19 presents the selected number, the programming of the processor is caused to retain the maximum value of X and display an inquiry concerning the maximum value of Y. The maximum value of Y is then similarly entered. Following entry of the maximum Y value, the processor will calculate the number of possible locations and compare that number with the number of locations available in the data store circuitry 18. Should the number be excessive, the processor will display a request that the operator select different value for X and Y. If the product of maximum X and maximum Y does not exceed available memory locations, then the gauge will ask for a site identification number. Such a site identification number is for user information only, and will permit subsequent correlation of the registered signals in the programmable memory device with the specific area which has been surveyed.

Upon the next operation of the start switch, the site identification number and the maximum X and maximum Y values are stored in a Random Access Memory (RAM) in the data storage circuitry 18 and the processor circuitry 16 through the display 19 indicates the coordinates of the first predetermined location at which the physical characteristic of density is to be measured. That is, the display 19 would indicate 1, 1. The operator is then to position the gauge at location 1, 1, and initiate the step of measuring the density of soil at that point by closing a start switch 20, 21. As measurement continues, a digital signal representative of the measured density is generated within the circuitry of the gauge and, under the control of programming steps performed within the processor 16, entered into the RAM in the data storage circuitry 18 and displayed on the display 19. In the specific example given, the detection of gamma photons of specific energy levels, and the counting of detected gamma photons, together with the calculation of density data for measured counts, are believed within the understanding of persons appropriately skilled in the applicable arts and will not here be discussed in great detail.

Upon completion of the measurement and registration of the generated signal in the RAM, the processor 16 through the display 19 will indicate that data is to be taken from another location. In an operating embodiment of a gauge in accordance with the present invention, the indication takes a form of an incrementing of the location coordinates in the X direction first, so that the indicated second location would be (2, 1). The programming operative within the processor 16 will attend to the successive locations at which the steps of measuring, generating and registering occur, so as to build in an orderly manner in RAM, a file of data.

Upon occasion, when surveying an area, it may become necessary to avoid a specific array location, or delete the reading otherwise possibly taken or to be taken at a specific location. Should that occur, the programming operative within the processor 16 will accommodate deletion of a specific location. By signaling through the input/output circuitry 15 to the processor 16, an X or Y coordinate offset may be indicated. Through use of the increment switch 24 and the decrement switch 22, the indicated value for one or both of the coordinate locations (X, Y)=(n, n) may be modified so as to reestablish a proper location in the array on an alternate side of the location at which no reading is to be taken. In an operating embodiment of the present invention, the programming within the processor 16 assumes that the operator wishes only to avoid reading at a single location, and will not permit resumption of measuring, generating and registering a generated signal until such time as normal gauge operation has been restored by appropriate signals.

The programming operable within the processor 16 may additionally provide for insertion of a newly generated signal with respect to a specific location. With such operation, any questionable signal generated during the course of a survey may be replaced. In such a sequence, programming within the processor 16 may be entered in a manner similar to that provided for avoiding a specific location, while indicating that the move is not to a new location. An indication that the move is not to a new location will be followed by a displayed inquiry from the processor 16 as to whether new data is to be registered. A signaled affirmative or "yes" will permit use of the increment switch 24 and decrement switch 22 to identify the specific location at which the registering of a previously generated signal is to be replaced by the registering of a newly generated signal. Measurement at the specifically identified location may then be completed.

As will be noted from the discussion given above, the step of registering a generated signal in a programmable memory device, in accordance with the present invention, comprises first filing the generated signals in RAM. As the survey of an area is completed, the file built by registering the signals in RAM may be transferred under the control of the processor 16 into the EPROM, which is a discrete, separable memory device. Once transferred, the file of signals will be retained by the EPROM indefinitely, until such time as the EPROM is erased through the use of ultraviolet light or as otherwise provided for the particular device chosen. The file generated can be closed at any time, by signaling to the processor 16 that the end of the file has been reached.

Thereafter, if appropriate, the discrete, separable memory device provided by the EPROM may be removed from the gauge and transported from the area surveyed to a remote location at which the file of registered signals retained within the EPROM may be retrieved and processed. With such retrieval and processing, and particularly with the use of computers equipped with plotters as peripheral devices, a directly readable map having the areas identified by soil density detected may be plotted, in a manner which will be appreciated by persons with appropriate skill in the applicable computer technology arts. Alternatively, numerical measurement values may be entered and displayed graphically at the specific locations in the array.

As pointed out briefly hereinabove, it is contemplated that the transmittal of data may be accomplished in alternative ways. Thus, an operator of the gauge 10 may be provided with a PROM reader, to which the EPROM may be transferred. The PROM reader may communicate, through a MODEM or the like, with a remote central processor capable of retrieving and processing the registered signals retrained within the EPROM. Alternatively, such a communication link may be connected directly with an appropriate socket 27 or the like provided on the gauge 10 as an output port from the processor circuitry 16. Where an appropriate central processing unit and graphic plotter are provided, such transfer and mapping may be accomplished directly and immediately in the field. It is believed that, with these suggestions in mind, persons of appropriate skill in the applicable arts of electronic data processing will be able to appreciate the alternatives made available by the present invention.

As briefly pointed out hereinabove, it is contemplated that the present invention is applicable to surveys of the type described with reference to other physical characteristics such as moisture content and thickness. With respect to moisture content, such surveys may be conducted for agricultural fields undergoing irrigation, as well as for construction sites where soil moisture may be a factor. With respect to thickness, such surveys might, by way of example only, extend to the thickness of paving materials applied in paving construction sites. Such measures may also apply to the thickness of sheets, films and the like. Additionally, while the registering of signals primarily on a location basis has been described, it is contemplated that signals might be registered over intervals of time. Thus, the "mapping" developed by practices in accordance with the present invention might present data concerning the change in moisture content or thickness within a defined area and over intervals of time. Particularly where irrigation of agricultural fields is concerned, the substantially simultaneous generation of displays identifying soil moisture changes over time may prove to be of significant benefit to those overseeing agricultural practices in the field being surveyed.

In the drawings and specification, there has been set forth a preferred embodiment of the invention, and although specific terms are employed, they are used in a generic and descriptive sense only and not for purposes of limitation.

That which is claimed is:

1. A method of surveying an area for variation in a physical characteristic effective for modifying nuclear radiation of a predetermined type, said method employing a nuclear radiation gauge which measures the modification of nuclear radiation of said predetermined type and a programmable memory device for storing digital information, said method comprising the steps of:
   (a) placing the nuclear radiation gauge at a predetermined location within a predetermined array on the area to be surveyed,
   (b) generating a digital signal representative of the measured characteristic at that location and registering the signal in said programmable memory device,
   (c) genrating a signal indicative of the next successive location within the predetermined array at which the step of signal generating and registering is to be repeated and displaying to an operator the indicated next successive location,
   (d) moving the gauge to the indicated next successive location, and
   (e) repeating steps (b), (c), and (d) at the next successive location within the predetermined array.

2. A method according to claim 1 further comprising the step of selectively overriding an indicated and displayed location selection and identifying in the programmable memory device an alternative predetermined location at which the steps of generating and registering occur.

3. A method according to claim 1 further comprising the steps of identifying a specific location at which the registering of a previously generated signal is to be replaced by the registering of a newly generated signal, and then repeating the steps of generating and registering the signal at the identified location and registering the newly generated signal in the programmable memory device.

4. A method of mapping a physical characteristic in an area, wherein the physical characteristic to be mapped is capable of modifying nuclear radiation of a predetermined type, said method employing a nuclear radiation gauge which measures the modification of nuclear radiation of said predetermined type and having a memory device for storing digital information, said method comprising the steps of:
   (a) subdividing the area to be mapped into an array consisting of a plurality of measurement locations,
   (b) placing the nuclear radiation gauge at a first predetermined location within said array on the area,
   (c) generating a signal representative of the measured characteristic at that location and registering the signal in the memory device,
   (d) moving the gauge to a succession of measurement locations within said predetermined array and at each successive location repeating the steps of generating a signal representative of the measured characteristic at that location and registering the signal in the memory device, and thereafter
   (e) retrieving from the memory device the registered signals representing the number of measurment locations and the measured cahracteristic at the respective measurement locations and processing the retrived signals in a memory device remote from the nuclear radiation gauge to generate therefrom a map display of the area and the physical characteristics thereof.

5. A method according to claim 4 wherein the step of registering the generated signal in a memory device comprises filing the generated signals in a first programmable memory device and subsequently transferring the file to a discrete, separable memory device, and further wherein the step of retrieving the registered signals from the programmable memory comprises separating the discrete, separable memory device from the gauge and transporting the separable memory device from the area surveyed to a remote area at which the steps of processing the retrieved signals and generating a map display are to be performed.

6. A method according to claim 4 wherein steps (b) through (c) are repeated at successive intervals of time for surveying the area for variation in a physical characteristic over time.

7. A nuclear radiation gauge for surveying an area for variations in a physical characteristic capable of modifying nuclear radiation at a plurality of measurement locations arranged in a predetermined array on the area, said gauge comprising:
nuclear radiation means for emitting nuclear radiation of a type selected as being susceptible to modification by the physical characteristic to be surveyed,
nuclear radiation detector means mounted in predetermined spaced relation to the source means for detecting nuclear radiation resulting from modification of radiation emitted from said source means and for generating signals representative of the physical characteristics of a location at which the gauge is positioned within the area, signal registering and storing means operatively connected with said detector means and responsive to generated signals for registering a signal representative of the physical characteristics of the material at a predetermined location at which the gauge is positioned within the area, said last named means including a programmable memory means for storing registered signals generated during a succession of measurements, and signal transmitting means operatively communicating with said programmable memory means for transmitting registered signals stored therewithin for retrieval and processing at a location remote from the gauge.

8. A gauge according to claim 7 wherein said signal transmitting means comprises a discrete, separable memory device for storing a file of registered signals generated at a succession of locations at which the gauge is successively positioned and removable from said gauge where subsequent retrieval and processing of the registered signals at the remote location.

9. A gauge according to one of claims 7 or 8 and further wherein said signal registering and storing means comprises processor means operatively connected for responding to the registration of a generated signal in a programmable memory device by generating a signal indicative of a next successive location distributed in a predetermined array within the area and at which the gauge is to be positioned.

10. A gauge according to claim 9 wherein said processor means includes means capable of selectively overriding an indicated and displayed location selection while identifying in the programmable memory means an alternative predetermined location at which the gauge is positioned.

11. A gauge according to claim 9 wherein said processor means is operatively connected for identifying a specific location at which the registration of a previously generated signal is to be replaced by the registering of a newly generated signal upon the gauge being positioned at the identified specific location.

12. A nuclear radiation guage for surveying an area for variations in a physical characteristic capable of modifying nuclear radiation, at a plurality of measurement locations arranged in a predetermined array on the area, said gauge comprising:

(a) nuclear radiation source means for emitting nuclear radiation of a type selected as being susceptible to modification by the physical characteristic to be surveyed, (b) nuclear radiation detector means mounted in predetermined spaced relationship to said source means for detecting nuclear radiation resulting from modification of radiation emitted from said source means and for generating signals representative of the physical characteristics of a predetermined location at which the gauge is positioned on within the area, and (c) signal registering and storing means operatively connected with said detector means and responsive to generated signals for registering a signal representative of the physical characteristics at the location at which the gauge is positioned, said signal registering and storing means including a programmable memory means having means for storing the registered signals generated at each of the successive measurement locations at which the gauge is successively positioned, means for indicating to the programmable memory means a measurment location where an obstruction exists and a measurement thus cannot be made and for identifying in the programmable memory device an alternative measurement location where the measurement is to be made, and means for transferring the stored signals taken from the measurement locations to a location remote from the moisture gauge for subsequent processing of the registered signals at a remote location.

* * * * *